United States Patent
LaRose

(10) Patent No.: US 9,849,223 B2
(45) Date of Patent: Dec. 26, 2017

(54) SILVER MOTOR STATOR FOR IMPLANTABLE BLOOD PUMP

(71) Applicant: HeartWare, Inc., Miami Lake, FL (US)

(72) Inventor: Jeffrey A. LaRose, Sunrise, FL (US)

(73) Assignee: HeartWare, Inc., Miami Lakes, FL (US)

( * ) Notice: Subject to any disclaimer, the term of this patent is extended or adjusted under 35 U.S.C. 154(b) by 94 days.

(21) Appl. No.: 13/891,785

(22) Filed: May 10, 2013

(65) Prior Publication Data
US 2013/0303833 A1    Nov. 14, 2013

Related U.S. Application Data

(60) Provisional application No. 61/646,028, filed on May 11, 2012.

(51) Int. Cl.
*A61M 1/12*    (2006.01)
*A61M 1/10*    (2006.01)
*A61N 2/00*    (2006.01)

(52) U.S. Cl.
CPC ............. *A61M 1/101* (2013.01); *A61N 2/002* (2013.01); *A61M 1/1025* (2014.02); *A61M 1/1031* (2014.02); *A61M 1/122* (2014.02); *A61M 1/125* (2014.02)

(58) Field of Classification Search
CPC ............................ A61M 1/101; A61M 1/1012
See application file for complete search history.

(56) References Cited

U.S. PATENT DOCUMENTS

| | | | | |
|---|---|---|---|---|
| 3,157,181 A | * | 11/1964 | McCarty | A61N 1/0551 607/118 |
| 3,602,745 A | * | 8/1971 | Davis | H02K 41/025 310/13 |
| 4,957,504 A | | 9/1990 | Chardack | |

(Continued)

FOREIGN PATENT DOCUMENTS

| | | |
|---|---|---|
| JP | S59-177059 A | 10/1984 |
| JP | S62-61144 U | 4/1987 |

(Continued)

OTHER PUBLICATIONS

International Search Report issued by the International Searching Authority (ISA/US) dated Aug. 15, 2013 in connection with International Application No. PCT/US2013/040590.

(Continued)

*Primary Examiner* — Michael Kahelin
(74) *Attorney, Agent, or Firm* — Christopher & Weisberg, P.A.

(57) ABSTRACT

In one embodiment of the present invention, an implantable blood pump includes a housing defining a flow path, a rotor positioned within the flow path, and a motor including a stator, positioned outside of said housing, the stator including a length of silver wire, wherein the silver wire is not positioned within a hermetically sealed compartment once the blood pump is ready for implantation into a patient in need thereof. The present invention may also include a method of implanting the implantable blood pump including the step of implanting the blood pump within the patient and within or adjacent to the vasculature.

13 Claims, 2 Drawing Sheets

(56) References Cited

U.S. PATENT DOCUMENTS

| | | | |
|---|---|---|---|
| 5,527,159 A | 6/1996 | Bozeman, Jr. et al. | |
| 5,695,471 A * | 12/1997 | Wampler | A61M 1/101 417/423.1 |
| 6,042,347 A | 3/2000 | Scholl et al. | |
| 6,183,412 B1 | 2/2001 | Benkowski et al. | |
| 6,293,901 B1 | 9/2001 | Prem | |
| 7,575,423 B2 | 8/2009 | Wampler | |
| 2011/0311383 A1 | 12/2011 | White | |

FOREIGN PATENT DOCUMENTS

| | | | |
|---|---|---|---|
| JP | 2002-532047 A | 9/2002 |
| JP | 2004-073725 A | 3/2004 |
| JP | 2007-535984 A | 12/2007 |
| JP | 2010-525871 A | 7/2010 |

OTHER PUBLICATIONS

Written Opinion of the International Searching Authority issued by the International Searching Authority (ISA/US) dated Aug. 15, 2013 in connection with International Application No. PCT/US2013/040590.

Office Action dated Jan. 27, 2017, issued by Japanese Examiner in corresponding Japanese Application Serial No. 2015-511767, filed May 10, 2013 (12-pages).

Extended European Search Report for Application No. EP 13787417 dated Dec. 11, 2015.

* cited by examiner

SILVER MOTOR STATOR FOR IMPLANTABLE BLOOD PUMP

CROSS-REFERENCE TO RELATED APPLICATIONS

The present application claims the benefit of the filing data of U.S. Provisional Patent Application No. 61/646,028, filed May 11, 2012, the disclosure of which is hereby incorporated herein by reference.

BACKGROUND OF THE INVENTION

Implantable blood pumps are typically used in the later stages of heart disease or after trauma to the heart, when the heart itself is too weak or otherwise incapable of creating sufficient blood pressure and blood circulation to satisfy body function.

Various blood pumps are already in use for the purpose of augmenting or replacing the blood pumping action of damaged or diseased hearts. Blood pumps are commonly used in three situations: (1) for acute support during cardio-pulmonary operations; (2) for short-term support while awaiting recovery of the heart from surgery; or (3) as a bridge to keep a patient alive while awaiting heart transplantation. The pumps may be designed to provide at least one of right or left ventricular assist, although left ventricular assist is the most common application in that it is far more common for the left ventricle to become diseased or damaged than it is for the right ventricle.

Implantable blood pumps comprise miniaturized pumps capable of being percutaneously or surgically introduced into or adjacent to the vascular system of a patient, typically to provide left or right heart support, or even total heart support. Various types of blood pumps include radial flow centrifugal pumps and axial flow pumps. Such pumps typically use magnetic or electromagnetic forces, for example, to power a magnetic rotor placed within or adjacent to a flow path of blood moving into or out of the heart. An at least one electromagnet, or stator, is positioned around the outside of a tubular casing containing the flow path, whereas the rotor is disposed inside the casing.

The rotor is magnetic. The stator typically is a set of electrically conductive wire coils. The rotor is energized by a power source with alternating currents through the coils to create a rotating magnetic field. That is, the field is directed transverse to the axis of the tubular casing, and the direction of the field rotates about the axis of the casing. As the field rotates, the rotor spins about its axis thus advancing the blood within the flow path. The power source may be implanted somewhere within the body of the patient or may be external to the patient, as is known in the art.

One such pump, disclosed in U.S. Pat. No. 7,575,423, the entirety of which is incorporated by reference herein as if fully set forth herein, is a centrifugal-type pump. FIGS. 3 and 7 of U.S. Pat. No. 7,575,423 have been reproduced herein as FIGS. 1 and 2, and illustrate a centrifugal-type implantable blood pump including a housing 14, defining the flow path for blood passing through the device. This device also includes a stator 56 having a metal wire coil or winding 57. A common metal used in such stators is copper wire. Around the stator is a second housing 12 which forms a seal around the stator and, once the pump is implanted into a patient in need thereof, prevents surrounding body fluids from contacting the stator.

While current implantable blood pumps provide numerous benefits to patients in need thereof, improvement can be made to the current devices to provide additional benefits to patients, in addition to potentially making such devices available to an even wider range of patients in need thereof.

BRIEF SUMMARY OF THE INVENTION

In one embodiment of the present invention, an implantable blood pump includes a housing defining a flow path, a rotor positioned within the flow path, and a motor including a stator, positioned outside of said housing, the stator including a length of silver wire, wherein the silver wire is not positioned within a hermetically sealed compartment once the blood pump is ready for implantation into a patient in need thereof.

The stator of this blood pump may be open to direct contact with body fluids. The blood pump of this embodiment may be a centrifugal-type radial flow blood pump, a radial-flow type blood pump, or the like. Further, the silver wire may be substantially surrounded by an insulation covering.

The present invention may also include, in another embodiment, a method of implanting the implantable blood pump including the step of implanting the blood pump within the patient and within or adjacent to the vasculature. Further, upon implanting the blood pump, the silver wire contacts a body fluid. The blood pump may be implanted within the heart, through the wall of the heart, adjacent to the heart, or the like.

In another embodiment, the present invention may include an implantable blood pump including a housing, a rotor mounted for rotation within said housing; a motor including an at least one stator disposed on the outside of said housing and mounted on said housing; said stator including a silver wire coil, wherein the stator is not positioned within a hermetically sealed compartment once the blood pump is ready for implantation into a patient in need thereof.

Further, the at least one stator may include two stators. Moreover, the at least one stator may include three or more stators.

DETAILED DESCRIPTION

The term "implantable blood pumps" as used throughout, is intended to refer generally to blood pumps which may be used within the vasculature, such as within the heart, through the wall of the heart, the aorta, the various arteries or veins, or the like, or adjacent to the vasculature, such as adjacent to the wall of the heart or within the abdomen adjacent to the heart or other vasculature. Typically, such blood pumps are implanted into the left or right ventricle of the heart. One such example of an implantable blood pump may be a ventricular assist device (VAD) or other pump which is implantable into a patient in need thereof.

Figure 3:
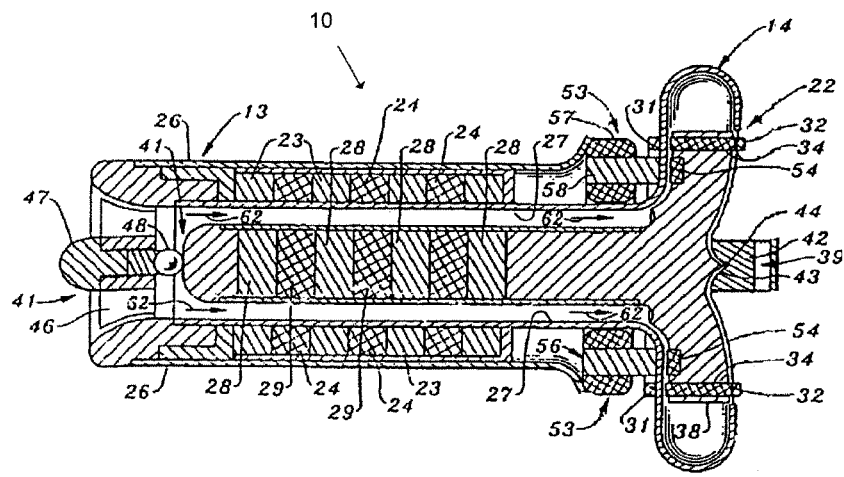
FIG. 3 illustrates one embodiment of the implantable blood pump of the present invention.

As illustrated in FIG. 3, in one embodiment, an implantable blood pump 10, illustrated as a centrifugal-type radial flow blood pump, includes a motor including a stator 56 having a length of metal wire 57 wound into a coil. The device 10 also includes housing 14 defining a flow path 62 therethrough. A rotor 17 (best seen in FIG. 1) is positioned within housing 14.

Figure 1:
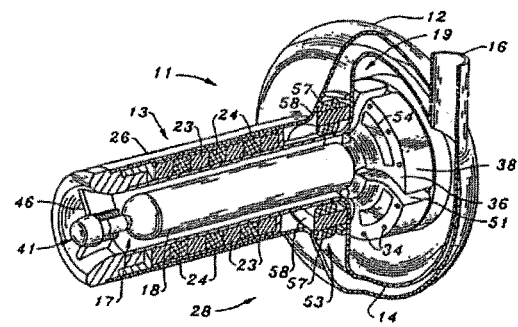
FIGS. 1 and 2 illustrate an implantable blood pump as known in the prior art.
Figure 2:
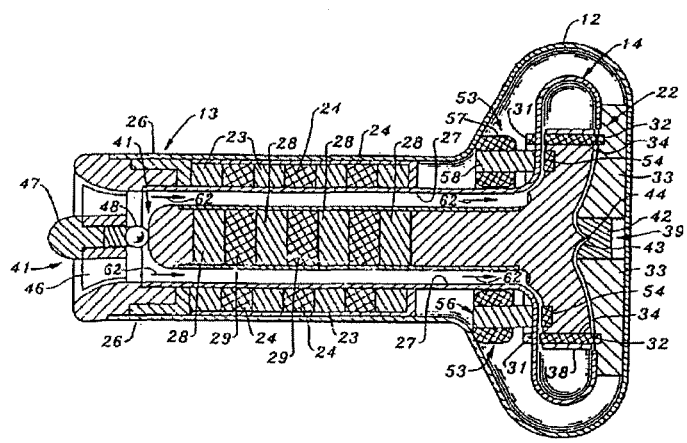

Contrary to the prior art blood pump of FIGS. 1 and 2, however, the device of the present invention does not include the housing 12. Housing 12 of FIGS. 1 and 2 would, once ready for implantation, create a seal which prevented intrusion of outside elements, such as body fluids, from entering the volume within housing 12 such that the stator, including the wire coils, would not come into contact with the body fluids. Such a housing 12 was necessary to prevent contact between the copper wire of the stator and the body fluids surrounding the implanted blood pump during the entire lifetime of the pump. A seal which prevents body fluids from entering the housing 12 and contacting the stator throughout the life of the blood pump is referred to herein as a hermetic seal.

Blood pump 10 in the embodiment of FIG. 3 includes metal wire 57 comprised of silver wire. The use of silver wire may eliminate the need for a secondary housing (such as housing 12) and as such, the need for a sealed compartment around the stator. In effect, the use of silver wire in stator 56 allows for contact between the stator and surrounding body fluids, upon implantation of the blood pump 10 into the patient in need thereof, to occur. Therefore, a seal, such as a hermetic seal for example, is not present in pump 10, once the pump 10 is ready for implantation, and is further not required in the embodiment of FIG. 3.

The silver wire 57 of stator 56 of this embodiment may be a length of silver wire, preferably a continuous length of silver wire, wound into a coil around a pole piece (not shown) or other material as known in the art. In this embodiment, the silver wire is a conventional wire, i.e., a discrete filament of silver. The silver wire 57 may also include an insulation covering to maintain separation of adjacent portions of the length of wire upon formation of the coil which may maintain proper electrical flow through the length of the wire. However, such insulation covering is not intended to prevent contact between the silver wire of the stator and the body fluids surrounding the implanted blood pump, and specifically such insulation covering is not intended to prevent contact between the silver wire of the stator and body fluids throughout the life of the pump 10.

Such silver wire 57, rather than a discrete filament, may also have a structure similar to, for example, a conductor on a circuit board. In one example, such a structure may be similar to a printed circuit board in that a silver length of material may form a conductive pathway along a non-conductive substrate. The silver conductive pathway may be laminated onto the non-conductive substrate in a coil pattern, or the like, and positioned within the pump 10 as a stator 56. Thus, as used in this disclosure, the term "wire" includes a conductor disposed on a dielectric substrate.

FIG. 3 illustrates a single stator 56 positioned on housing 14. However, pump 10 may have more than one stator, and thus may have two stators, three stators, or more than three stators. In the embodiment of pump 10 having three stators 56, such stators would be positioned circumferentially around housing 14, and mounted on the outside surface of housing 14, and a central portion of each stator preferably would be positioned substantially equidistant from one another (e.g., about 120 degrees from one another relative to a central longitudinal axis of pump 10). Depending on the size of each stator, a portion of each stator may overlap a portion of either or both adjacent stators.

Figure 4:
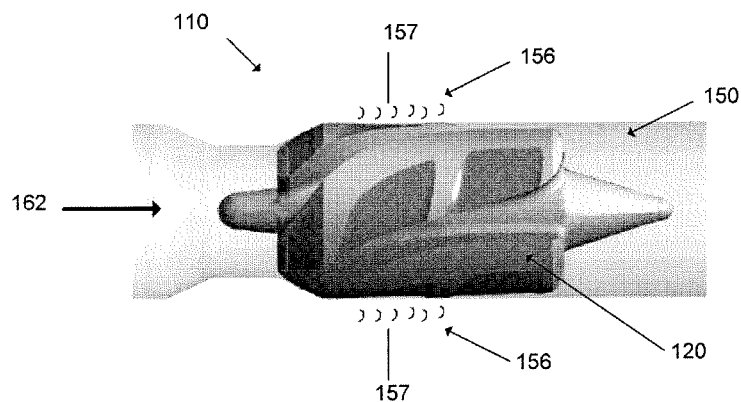
FIG. 4 illustrates another embodiment of the implantable blood pump of the present invention.

While FIG. 3 illustrates a centrifugal-type implantable blood pump 10, silver wire coils may be used in stators in other types of blood pumps, including axial-flow type blood pumps, such as the pump disclosed in U.S. application Ser. No. 13/163,253, published as U.S. Publication No. 2011/0311383, the entirety of which is incorporated by reference herein as if fully set forth herein. FIG. 4 illustrates such an implantable blood pump 110. In this embodiment, the pump 110 includes a rotor 120 positioned within a housing 150 having a flow path 162, a motor including an at least one stator 156 disposed on the outside of housing 150 and mounted on housing 150, and the stator 156 includes an electrically conductive length of silver wire 157 coiled around a pole piece or like substrate (not shown). The pump 110 includes at least one stator 156, or, as illustrated, the pump 110 may include two stators substantially equidistant from one another—one on one side of the housing and another on an opposite side of the housing (e.g., about 180 degrees from one another relative to a central longitudinal axis of pump 110). Depending on the size of each stator, a portion of each stator may overlap a portion of either or both adjacent stators. Such equidistant positioning of the stators may allow for more efficient and smoother operation of the rotor.

In an alternative arrangement, pump 110 may include at least three stators positioned circumferentially around the housing substantially equidistant from one another (e.g., about 120 degrees from one another relative to a central longitudinal axis of pump 110). Depending on the size of each stator, a portion of each stator may overlap a portion of either or both adjacent stators.

As above, the stator silver wire coils 157 are positioned outside of the housing 150 and thus are not within a sealed volume (e.g., within a second, outer housing) and are therefore open to direct contact with body fluids upon implantation of device 110 into a patient in need thereof. Also, as above, the silver wire 157 of this embodiment may optionally include an insulation covering to maintain separation of adjacent portions of the length of wire upon formation of the coil which may maintain proper electrical flow through the length of the wire. However, such insulation covering is not intended to prevent contact between the silver wire of the stator and the body fluids surrounding the implanted blood pump, and specifically such insulation covering is not intended to prevent contact between the silver wire of the stator and body fluids throughout the life of the pump 10.

In another embodiment, the present invention may include a method of implanting the implantable blood pump 10, 110 including accessing the interior of a patient in need thereof and implanting the blood pump 10, 110 within the patient in communication with the vasculature. The blood pump 10, 110 may be implanted within the vasculature, such as within the heart, through the wall of the heart, within the aorta, within the various arteries or veins, or the like; or adjacent to the vasculature, such as adjacent to the wall of the heart or within the abdomen adjacent to the heart or other vasculature. Once implanted, the silver wire of the stator may come into contact with body fluids. In arrangements of this method where the blood pump itself is not implanted within the vasculature, the method may include the further step of implanting a conduit from the pump to the vasculature to create a flow path for the blood to pass between the pump and the vasculature. Typically, blood pump 110 (FIG. 4) is implanted within the vasculature, while blood pump 10 (FIG. 3) is commonly implanted either through the wall of the heart or adjacent to the vasculature.

Numerous benefits may be realized with the use of silver wire in the stator. For example, the use of silver wire may eliminate the need for a seal, for example a hermetic seal, to be placed around the stator. Since silver is a biocompatible metal, the contact between bodily fluids and the silver wire is acceptable. Moreover, it is known that silver does not provide for a suitable substrate on which bacteria and other organisms can grow, thus leaving the silver wire open to body fluids should not provide any increased risk for infection of the surrounding anatomy or rejection of the device 10, 110 by the patient.

The elimination of the outer housing (and thus seal around the stator) may thus result in a device having smaller dimensions and a lighter weight than currently available implantable blood pumps. Such smaller and lighter pumps may be less invasive to the surrounding anatomy and thus make such pumps available to a greater number of patients, particularly, for example, those whose anatomy may not have the strength or capacity to support a larger blood pump.

Another potential benefit of the use of silver wire in the stator may relate to the conductivity of silver. Silver is a better conductor than other metals currently being used, such as copper ($6.3 \times 10^7$ siemens/meter vs. $5.96 \times 10^7$ siemens/meter (copper)). Thus, the use of silver rather than other metals may decrease the build-up of heat in the implanted pump due to its high conductivity and, inversely, its low resitivity.

Additionally, the increased conductivity and decreased resistance of silver may increase battery life. As most implantable blood pumps operate using a rechargeable battery pack, a patient using device 10, 110 may benefit from a longer length of time between charges of the battery pack, which may result in an increase in the patient's standard of living and independence.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implantable blood pump comprising:
   a housing defining a blood flow path and a longitudinal axis extending along the blood flow path;
   a rotor positioned within the blood flow path; and
   a motor including at least two stators positioned outside of the housing and each including a portion overlapping an adjacent stator and a silver wire forming a distalmost outer region of a portion of a blood pump relative to the longitudinal axis, the silver wire being configured to directly contact a body fluid when implanted within a patient.

2. The blood pump of claim 1, wherein the blood pump is a centrifugal-type radial flow blood pump.

3. The blood pump of claim 1, wherein the blood pump is an axial-flow type blood pump.

4. The blood pump of claim 1, wherein the silver wire is positioned as a coil on the outside of the housing and the silver wire is substantially surrounded by an insulation covering adapted to maintain separation of adjacent portions of the coil to maintain proper electrical flow and does not prevent contact of the silver wire with the body fluid.

5. The blood pump of claim 1, wherein the silver wire is a conductor pathway laminated onto a dielectric substrate.

6. A method of implanting an implantable blood pump, the method comprising:
   providing an implantable blood pump including:
      a housing defining a blood flow path and a longitudinal axis extending along the blood flow path;
      a rotor positioned within the blood flow path; and
      a motor including at least two stators positioned outside of the housing and each including a portion overlapping an adjacent stator and a silver wire forming a distalmost outer region of a portion of a blood pump relative to the longitudinal axis; and
   implanting the implantable blood pump into one of a heart and through a wall of the heart of a patient.

7. The method of claim 6, wherein upon implanting the implantable blood pump, the silver wire contacts a body fluid.

8. An implantable blood pump, comprising:
   a blood pump housing defining a blood flow path and a longitudinal axis extending along the blood flow path;
   a rotor mounted for rotation within the blood pump housing; and
   a motor including at least two stators mounted on an outside of the blood pump housing, the at least two stators each including a portion overlapping an adjacent stator and a silver wire coil forming a distalmost outer region of a portion of a blood pump relative to the longitudinal axis.

9. The blood pump of claim 8, wherein the pump is a centrifugal-type radial flow blood pump.

10. The blood pump of claim 8, wherein the pump is an axial-flow type blood pump.

11. The blood pump of claim 8, wherein the at least two stators includes at least three stators.

12. The blood pump of claim 8, wherein the silver wire coil is substantially surrounded by an insulating sheath adapted to maintain separation of adjacent portions of the coil to maintain proper electrical flow and permit contact of the silver wire with a body fluid.

13. The blood pump of claim 8, wherein the silver wire coil is a conductor pathway laminated onto a dielectric substrate.

* * * * *